(12) United States Patent
Kruspe et al.

(10) Patent No.: US 7,084,625 B2
(45) Date of Patent: Aug. 1, 2006

(54) METHOD AND APPARATUS OF REDUCING RINGING IN A NUCLEAR MAGNETIC RESONANCE PROBE

(75) Inventors: Thomas Kruspe, Wienhausen (DE); Arcady Reiderman, Houston, TX (US); Martin Blanz, Celle (DE); Peter Rottengatter, Isernhagen (DE)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 11/034,403

(22) Filed: Jan. 12, 2005

(65) Prior Publication Data

US 2005/0127909 A1 Jun. 16, 2005

Related U.S. Application Data

(63) Continuation of application No. 10/177,618, filed on Jun. 20, 2002, now Pat. No. 6,844,727, which is a continuation-in-part of application No. 09/605,463, filed on Jun. 28, 2000, now Pat. No. 6,452,388.

(51) Int. Cl.
*G01V 3/00* (2006.01)
*G01R 33/20* (2006.01)

(52) U.S. Cl. .................................................... 324/303

(58) Field of Classification Search ................ 324/303, 324/309, 338–339, 314, 346, 253, 249; 428/692; 343/787
See application file for complete search history.

(56) References Cited

U.S. PATENT DOCUMENTS

| | | | |
|---|---|---|---|
| 4,350,955 A | 9/1982 | Jackson et al. | 324/303 |
| 4,629,986 A | 12/1986 | Clow et al. | 324/303 |
| 4,710,713 A | 12/1987 | Strikman | 324/303 |
| 5,168,223 A | 12/1992 | Le Thiec | 324/253 |
| 5,220,338 A | 6/1993 | Matsushita | 343/787 |
| 5,220,339 A * | 6/1993 | Matsushita | 343/788 |
| 5,376,884 A | 12/1994 | Sezginer | 324/303 |
| 5,486,761 A | 1/1996 | Sezginer | 324/303 |
| 5,530,358 A | 6/1996 | Wisler et al. | 324/338 |
| 5,606,260 A | 2/1997 | Giordano et al. | 324/339 |
| 5,644,231 A | 7/1997 | Wignall | 324/303 |
| 5,712,566 A | 1/1998 | Taicher et al. | 324/303 |
| 5,757,186 A | 5/1998 | Taicher et al. | 324/303 |
| 6,069,479 A * | 5/2000 | Taicher et al. | 342/309 |
| 6,183,889 B1 | 2/2001 | Koshiba et al. | 428/692 |
| 6,215,304 B1 | 4/2001 | Slade | 324/303 |
| 6,232,775 B1 | 5/2001 | Naitoh et al. | 324/249 |
| 6,326,785 B1 | 12/2001 | Kruspe | 324/303 |
| 6,366,086 B1 | 4/2002 | Sen | 324/303 |

(Continued)

FOREIGN PATENT DOCUMENTS

GB 2141236 A 12/1984

OTHER PUBLICATIONS http://www.britannica.com/eb/print?eu=42785; hysteresis, Encyclopedia Britannica Article, pp. 1-2.

(Continued)

*Primary Examiner*—Diego Gutierrez
*Assistant Examiner*—Tiffany A. Fetzner
(74) *Attorney, Agent, or Firm*—Madan, Mossman & Sriram, P.C.

(57) ABSTRACT

The present invention provides a novel use of a material having a high internal magnetostrictive damping and/or using material with explicitly low magnetostriction as a NMR probe core material. The probe structural geometry facilitates the use of material, which has a relatively low magnetic permeability.

15 Claims, 8 Drawing Sheets

U.S. PATENT DOCUMENTS

| 6,445,187 | B1 | 9/2002 | Montgomery et al. | 324/346 |
| 6,452,388 | B1 | 9/2002 | Reiderman et al. | 324/303 |
| 6,844,727 | B1 * | 1/2005 | Kruspe et al. | 324/303 |
| 2003/0038631 | A1 | 2/2003 | Kruspe et al. | 324/303 |
| 2005/0127909 | A1 * | 6/2005 | Kruspe et al. | 324/303 |
| 2005/0248341 | A1 * | 11/2005 | Kruspe et al. | 324/303 |

OTHER PUBLICATIONS http://www.britannica.com/eb/print?eu=42785; magnetostriction, Encyclopedia Britannica Article, p. 1.

R.J. Edwards; *Transmitting Loop Antennas when the Perimeter is Less than 0.75 Wavelengths Long*, http://www.smeter.net/antennas/rjeloop2.php Dec. 18, 2005, pp. 1 and 2.

* cited by examiner

METHOD AND APPARATUS OF REDUCING RINGING IN A NUCLEAR MAGNETIC RESONANCE PROBE

CROSS-REFERENCES TO RELATED APPLICATIONS

This application is a continuation of U.S. patent application Ser. No. 10/177,618 filed on Jun. 20th, 2002, now the U.S. Pat. No. 6,844,727 B2, which is a continuation-in-part of U.S. patent application Ser. No. 09/605,463 filed on 28 Jun. 2002, which is now U.S. Pat. No. 6,452,388 B1, the contents of both of these patent references are fully incorporated herein by reference.

FIELD OF THE INVENTION

The present invention is related to the field of nuclear magnetic resonance ("NMR") sensing apparatus. More specifically, the invention is related to a NMR well logging apparatus having a powdered soft magnetic material core as a flux concentrator for sensing NMR properties within earth formations adjacent a wellbore.

DESCRIPTION OF THE RELATED ART

NMR well logging instruments can be utilized for determining properties of earth formations including: the fractional volume of pore space, the fractional volume of mobile fluid filling the pore space and other petrophysical parameters. An NMR well logging instrument typically contains a permanent magnet to generate a static magnetic field in adjacent earth formations. The NMR well logging instrument typically includes a transmitting antenna assembly positioned near the magnet. The transmitting antenna assembly is shaped so that a pulse of radio frequency (RF) power conducted through the antenna assembly induces a RF magnetic field in the adjacent earth formation. The induced RF magnetic field is generally orthogonal to the static magnetic field, thereby creating appropriate conditions for NMR excitation in the formation.

Following the RF antenna pulse, voltages representative of NMR conditions in the formation are induced in the receiving antenna. In particular, these voltages represent processional rotation of hydrogen or other nuclei spin axes about the static magnetic field generated by the NMR well logging tool. NMR apparatus designs typically use the same antenna for transmitting and receiving along with de-coupling, receiving and protection circuitry.

There are various known NMR well logging instruments proposed and/or implemented for measuring NMR properties of substances, in particular, the properties of earth formations. One type of NMR instrument is described in U.S. Pat. No. 4,710,713 ('713), by Taicher et al. Another type of NMR instrument is described in U.S. Pat. No. 4,350,955 ('955), by Jackson et al. Both of these NMR instruments represent early designs of well logging NMR instruments with the main focus on the magnet assembly. No provision was made in these early designs for the use of a soft magnetic material in the NMR probe for improving the efficiency of the RF antenna.

It was recognized in more recent NMR well logging tool designs that a soft magnetic material can be utilized as a magnetic flux concentrator to increase efficiency of generating and receiving RF signals. For example, the NMR well logging instruments using ferrite material as an essential element of the design are described in U.S. Pat. No. 5,712,566 ('566), by Taicher et al., in U.S. Pat. No. 5,644,231 ('231) by A. H. Wignall, in UK Patent Application GB 2 141 236 ('236) by A to H. Clow, et al. and in U.S. Pat. No. 5,376,884 ('884) by A. Sezginer.

All prior designs known to the present inventors, however, explicitly or implicitly suggest ferrite as the soft magnetic material satisfying the requirements of high permeability and negligible RF losses. Ferrite materials, however, suffer from a relatively low saturation flux density, typically in the range of 0.3–0.4 T. This relatively low saturation flux density results in core saturation when the ferrite core is placed near the NMR probe permanent magnet. NMR probe core saturation results in reduction of the core magnetic permeability which tends to increase core sensitivity to temperature variations. A sintered ferrite material core tends to generate magnetostrictive ringing in a strong RF magnetic field. Elimination of this parasitic magnetostrictive ringing signal increases the complexity and cost of NMR antenna design.

A common limitation of the '231, '566, '884, and '236 patent designs is the necessity of finding or creating a magnetic field low enough in a region where the soft ferrite material can be positioned to avoid saturation. For example, the apparatus disclosed in the '231 patent provides a soft magnetic ferrite material loaded in the antenna coil (a so called half-coax antenna). As described in the '231 patent, the effectiveness of the ferrite material is substantially reduced by the strong magnetic field of the permanent magnet. The structure of the '231 patent compensates for this reduction in effectiveness by providing a magnetic shield around the ferrite region. The shield comprises a shell of soft magnetic steel, which effectively provides a shunt path for static magnetic field in the region of the antenna. Implicitly, the steel shell is not saturated due to its sufficient saturation flux density and cross-sectional area. The necessity of creating a region of low static magnetic field places a serious constraint on the design of NMR probes. In particular it places limitations on the antenna core size, thereby reducing the efficiency of the antenna.

U.S. patent application, Ser. No. 09/605,463 of Reiderman et al teaches the use of a soft magnetic core as part of an antenna assembly. Included in the teachings is a discussion of magnetostrictive ringing and possible remedies to reduce the ringing. The discussion on magnetostrictive ringing did not fully investigate the possible causes of this ringing and only partially discussed methods and materials for its reduction.

An alternate approach to reducing magnetostriction uses non-metallic soft magnetic materials (ferrites) as taught by Prammer et al. (U.S. Pat. No. 6,268,726). Prammer discloses the use of 1 mm thick layers of ferrite in combination with 0.3 mm layers of rubber or lead filled epoxy. The arrangement taught by Prammer has increased complexity and an increase of flux density and an accompanying risk of saturation in the ferrite layers. As the amount of ferrite needs to be reduced in the same volume, the efficiency of the antenna core is reduced.

Yet another method to reducing the ringing on NMR signals caused by magnetostriction in an antenna core is to provide a condition of substantially zero static field at the core material. In a zero static magnetic field, an oscillating stress due to magnetostriction in a soft magnetic core produces substantially no changes in the net magnetization of the core. An NMR tool where this condition is satisfied is disclosed in U.S. Pat. No. 5,712,566 to Taicher and Reiderman. As taught therein, the antenna core is placed in a cylindrical hole at the center of a transversely magnetized magnet. While such a design is practical for wireline logging, it is difficult to do this with MWD logging tools.

U.S. patent application Ser. No. 09/605,463 of Reiderman et al (now U.S. Pat. No. 6,452,388) teaches the concept of using a soft magnetic material for an antenna core. However, the principles to be used in selecting suitable antenna core material for NMR applications were not fully explored therein.

Thus, there is a need for a NMR probe core material that overcomes the limitations of prior art discussed above following a further evaluation of principles for selection of the core material. The present invention satisfies this need.

SUMMARY OF THE INVENTION

The present invention is a nuclear magnetic resonance (NMR) logging apparatus for use in a borehole for determining properties of an earth formation surrounding the borehole. The apparatus comprises a magnet for inducing a static magnetic field in a region of interest in the earth formation. A transmitting antenna assembly is used for inducing a radio frequency magnetic field within the region of interest and producing signals from materials in the region of interest. A receiving antenna assembly is used for detecting said signals from said region of interest. At least one of the antenna assemblies includes a magnetic core formed from a material having high internal magnetostrictive damping and/or low magnetostriction. A suitable material having high internal damping is a non-conductive, powdered soft magnetic material having a grain size sufficiently small to reduce intragranular power loss at the operating frequency of the RF magnetic field. The magnetic material may further have a grain size less than half a wavelength of an acoustic wave at the frequency of the RF field.

A suitable material having high internal damping has a large area within a hysteresis loop associated with magnetostrictive deformation. A suitable material is an amorphous metal.

In an optional embodiment of the invention, the same antenna is used as both the transmitting antenna and the receiving antenna.

BRIEF DESCRIPTION OF THE DRAWINGS

The application is best understood with reference to the following drawings wherein like numbers in different figures refer to like components and in which.

DETAILED DESCRIPTION OF A PREFERRED EMBODIMENT

Figure 1:
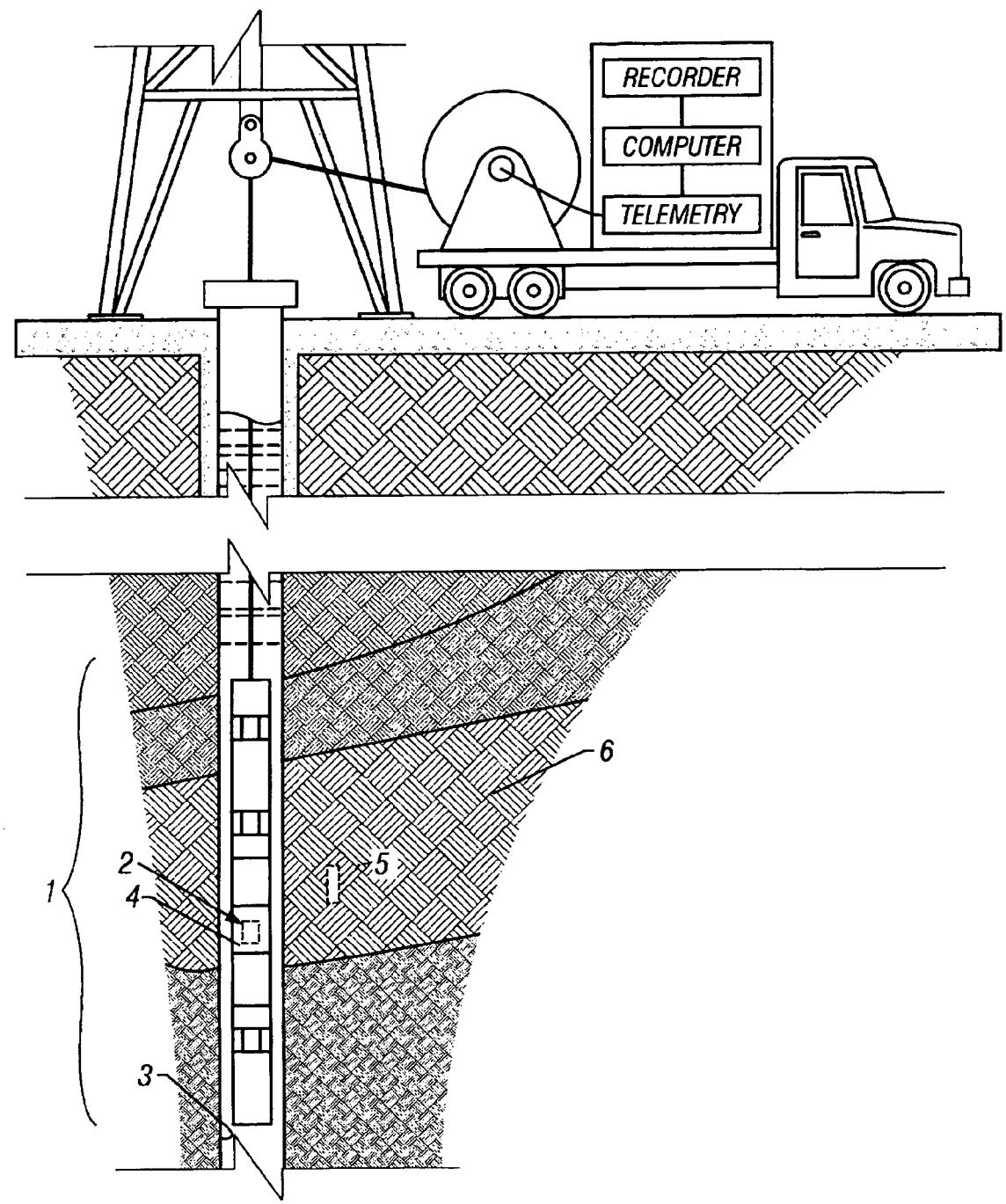
FIG. 1 (prior art) is an illustration of a typical NMR tool deployed in a bore hole.

FIG. 1, illustrates well logging tool string 1 having an NMR probe 2, having antenna assembly 4 deployed in bore hole 3. The NMR probe sends magnetic pulses into and receives signals from region of investigation 5 in formation 6. FIG. 1 is shown for purposes of showing an example of the orientation of a tool utilizing the present invention and is not intended to limit the use of the present invention to a particular application or orientation.

Figure 2:
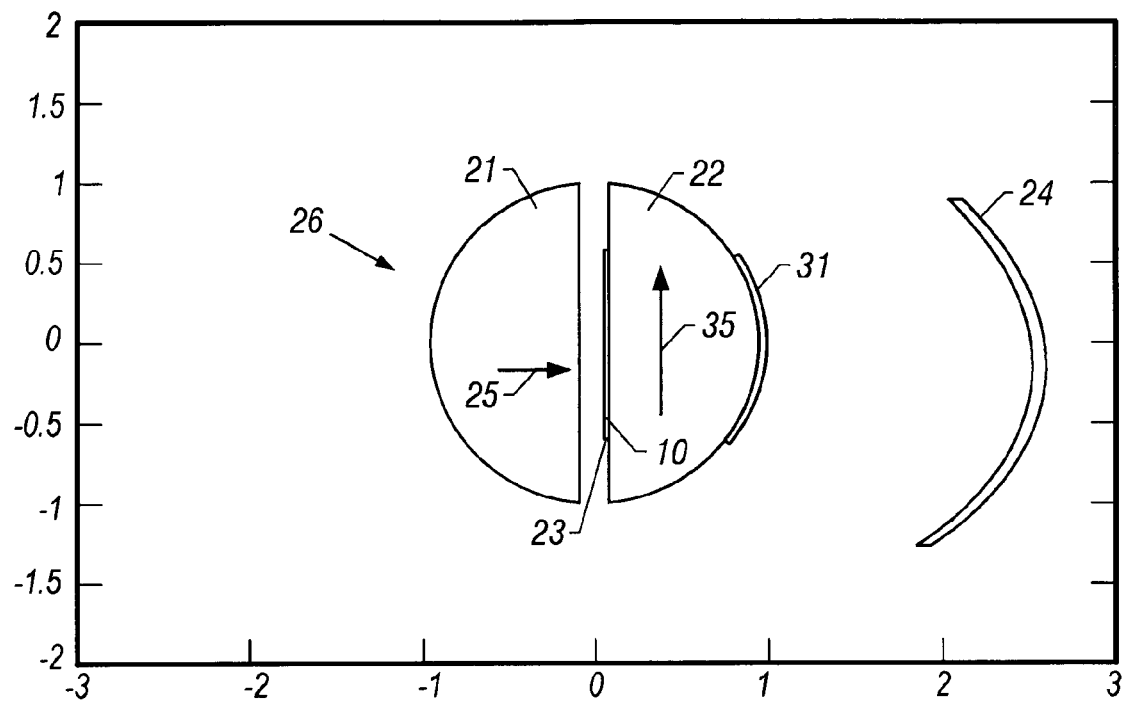
FIG. 2 (prior art) is a cross-sectional view of a preferred embodiment of the present invention illustrating the geometry of a preferred NMR probe using the preferred powdered soft magnetic material of the present invention.

FIG. 2 illustrates a cross section of an exemplary logging tool for use with the present invention, taken perpendicular to axis of elongation. The preferred embodiment of FIG. 2, comprises a probe 2, moveable through a bore hole 3 for measuring nuclear magnetic resonance (NMR) properties of a formation 6 surrounding the bore hole. The preferred probe comprises an elongated permanent magnet 21, having an axis of elongation extending parallel to the axis of elongation of the probe 2 and parallel to the longitudinal axis of the bore hole 3. The axes of elongation are perpendicular to plane of FIG. 2. Permanent magnet 21 has magnetic dipole moment 25 perpendicular to the axes of elongation.

Preferred antenna assembly 10 has an axis of elongation generally parallel to the axis of the magnet 21. The preferred antenna assembly 10 comprises soft magnetic core 22 and flat wires 23 and 31. Core 22 is preferably comprised of the preferred powdered soft magnetic material such as the commercially available MICROMETALS™ or FLUXTROL™ iron powder materials and preferably comprises a ferromagnetic metal powder combined with an organic non-conductive binder, such as an epoxy resin. The particle size of the powder is small enough to appear transparent to the RF magnetic field. In the 0.5–1.0 MHz frequency range, the preferred non-ferrite soft magnetic material exhibits acceptable RF losses, thereby causing negligible deterioration of the NMR antenna Q-factor. An alternative to the powdered soft-magnetic material is provided by a laminated stack of ferromagnetic material ribbons as flux guiding material. The ribbons made from soft-magnetic material, which have preferable a low magnetostriction, such as amorphous metal for instance METGLAS™, need to be isolated from each other. The orientation of the ribbons has to be in the direction of the magnetic flux and the thickness needs to be low compared to the skin-depth of the respectively frequency in order to minimize eddy-currents. Antenna assembly 10 has a magnetic dipole moment 35 in the plane perpendicular to the axis of elongation. The antenna dipole moment 35 is perpendicular to a line between the effective center of the magnet dipole moment 25 and the effective center of the antenna dipole moment. Thus, the antenna assembly 10 generates a RF magnetic field perpendicular to the magnetic field of the permanent magnet in the area in front of the probe in sensitive volume 24 which is defined by the magnetic field of the permanent magnet and the RF magnetic field parameters.

Specifically, the static magnetic field, for which the resonance condition exists, is proportional to the excitation and detection frequency of the apparatus; the proportionality factor (gyromagnetic ratio) is dependent on the kind of atomic nuclei used, e.g. protons (hydrogen nuclei). Similarly, the RF magnetic field have optimum amplitudes that are related to the RF pulse durations and a direction perpendicular to the static magnetic field.

For the preferred embodiment of the probe presented in FIG. 2, the sensitive volume 24 is close to the shape of an arc in a cross-sectional plane perpendicular to the axis of elongation, the arc extending within a defined angle, typically 70–120 degrees, depending upon the particular geometry of the magnet and the RF antenna assembly. Since the volume of investigation 24 exists on one side of the probe of FIG. 2, it is referred to as a side looking NMR probe design. The preferred core material, however, can be utilized in applications other than side looking probes or NMR applications for formations adjacent a bore hole.

The preferred probe core uses a non ferrite powdered soft magnetic material core which exhibits a lower magnetic permeability than sintered ferrite cores. The preferred powdered soft magnetic core material's permeability $\mu_m$ is typically 20–30, in contrast to permeability in the range of 500–1000, for ferrite NMR cores operating in the same frequency range. However, the preferred probe performs as effectively as a ferrite soft magnetic material as explained below.

For a given current in RF antenna elements 23 and 31, the antenna magnetic moment, and consequently the antenna RF magnetic field projected into the NMR volume of investigation 24 is proportional to the effective magnetic permeability $\mu$ of the preferred soft magnetic core. The effective magnetic permeability $\mu$ is calculated using the magnetic material permeability $\mu_m$ and a core demagnetizing factor, D as follows:

$$\mu = 1 + (\mu_m - 1)/((\mu_m - 1) \cdot D + 1)) \quad (1)$$

The demagnetizing factor can be estimated from the elliptic equivalent of the cross-section of the core 22, as shown in FIG. 2, as follows:

$$D = S_x/(S_x + S_y) \quad (2)$$

As shown in FIG. 2, in eqn. (2), Sx and Sy represent the elliptic equivalent dimensions in the horizontal and vertical dimensions respectively, in the plane of FIG. 2, for a preferred powdered soft magnetic material core 22 geometry. There are two limiting cases for equation (1), as follows:

$$(D)(\mu_m - 1) << 1 \text{ or } \mu = \mu_m; \text{ and} \quad (3)$$

$$(D)(\mu_m - 1) >> 1, \text{ which means } \mu \approx 1 + 1/D \text{(independent of } \mu_m\text{)}. \quad (4)$$

The second limit of eqn. (4) corresponds to the situation where the effective magnetic permeability and antenna efficiency are substantially independent of the magnetic permeability of the material. The maximum available permeability of the preferred, non-ferrite soft magnetic iron powder materials for the frequency around 1 MHz is about 20. If we require that D ($\mu_m$−1)>5, which means insignificant effective permeability loss compared to high permeability ferrite, then the effective permeability as defined by the equation (1) should be less than 5. This value for the effective permeability corresponds to the demagnetizing factor of more than 0.25 and the $S_y/S_x$ ratio of less than 3.

In a preferred embodiment, using the preferred powdered soft magnetic material, a magnetic core shape is provided, having values for $S_x$ and $S_y$, which ensure that the effective permeability of the core, $\mu$ as determined by the core proportions associated with the shape or core geometry does not exceed a value of 5. It is these relative proportions, rather than a particular shape that facilitate use of the preferred powder core material. For known prior core geometric shapes, structures or designs, the effective magnetic permeability, dictated by the core shape, is greater than 5, which renders the preferred non ferrite powder soft magnetic material ineffective when compared to the performance of ferrite cores.

Figure 3:
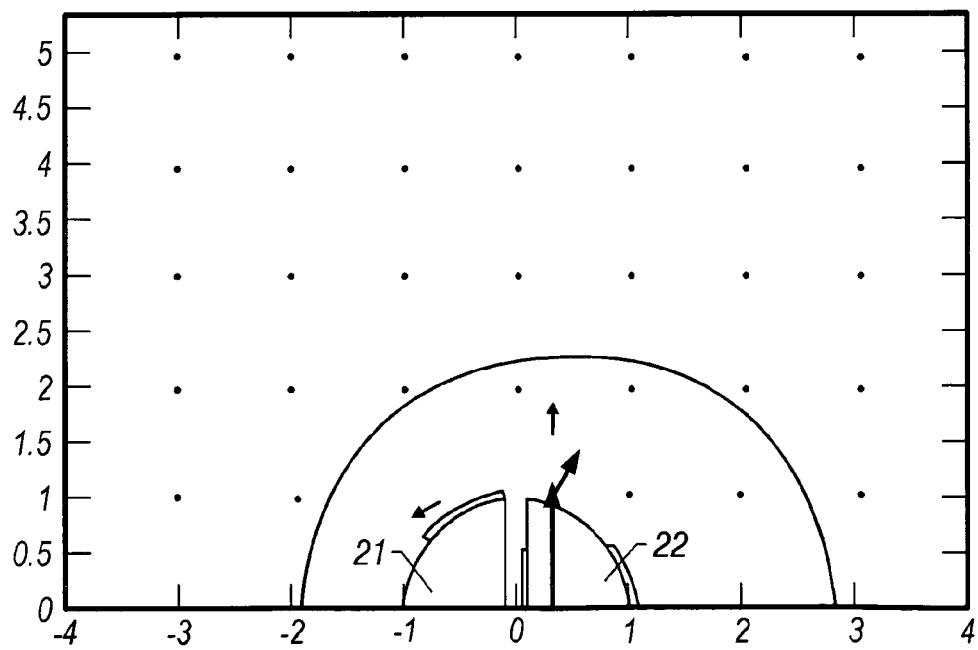
FIG. 3 (prior art) is a plot of the isoline for the RF field generated by a preferred embodiment of the present invention utilizing a powdered soft magnetic core.
Figure 4:
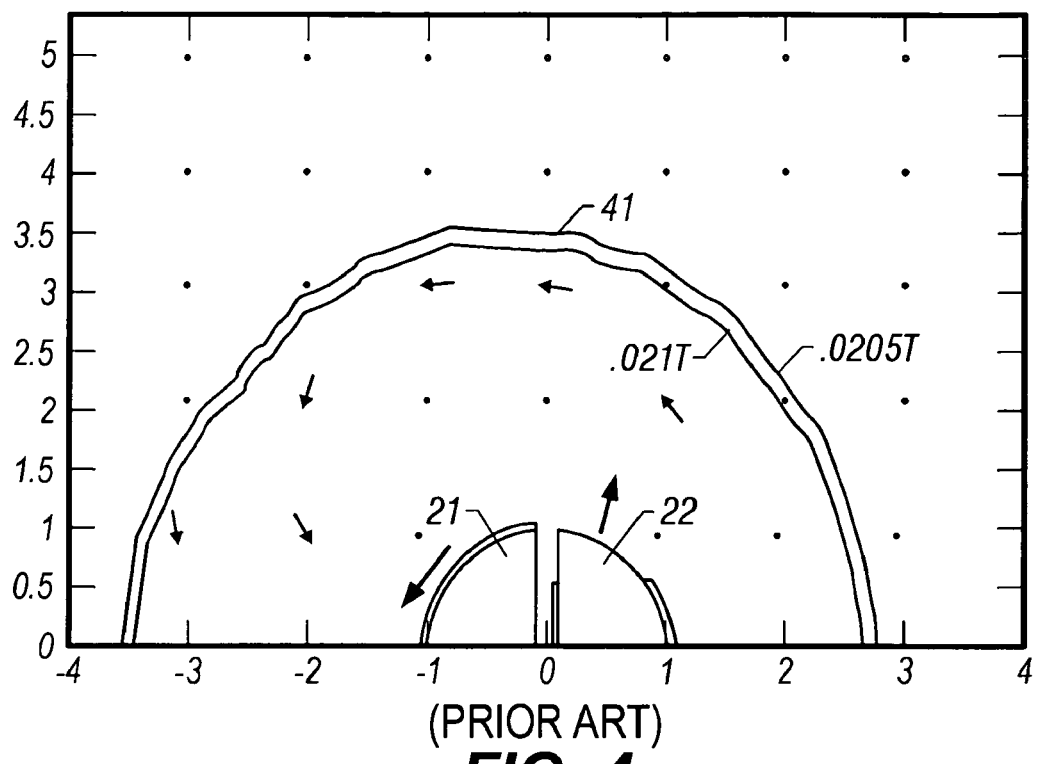
FIG. 4 (prior art) is a plot of two isolines for the static field generated by a preferred embodiment of the present invention utilizing a powdered soft magnetic core.
Figure 5:
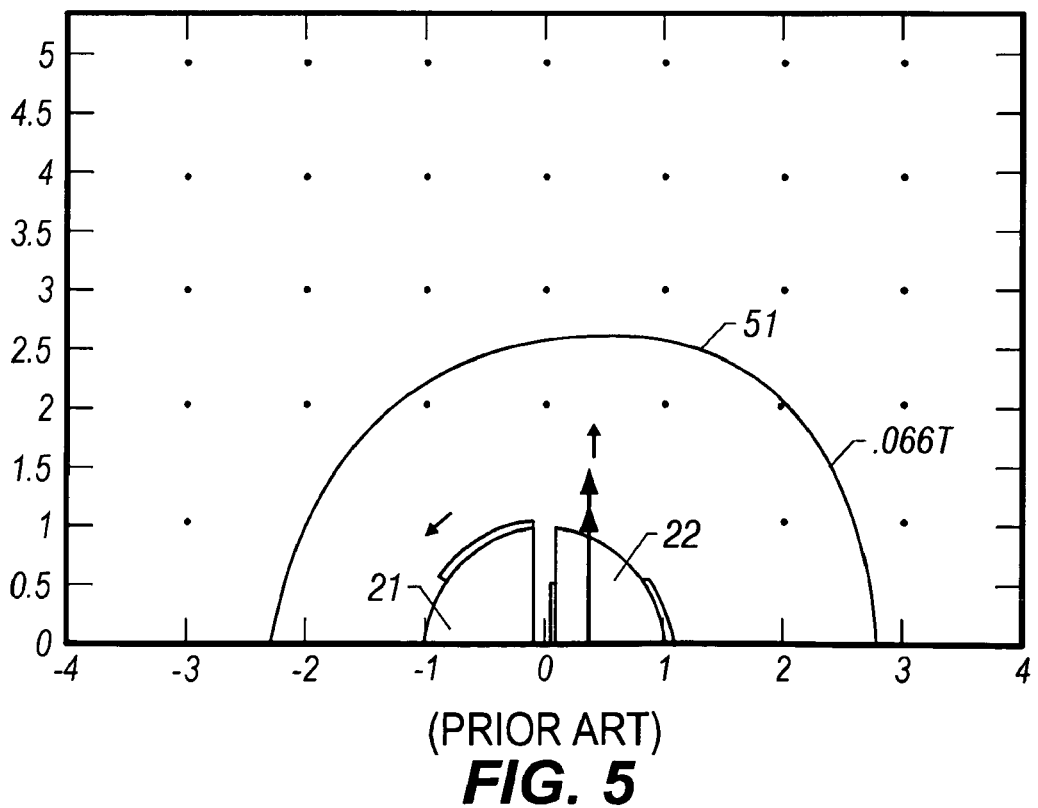
FIG. 5 (prior art) is a plot of the isolines for the RF field generated by the probe geometry of FIG. 2 without utilizing a powdered soft magnetic core.
Figure 6:
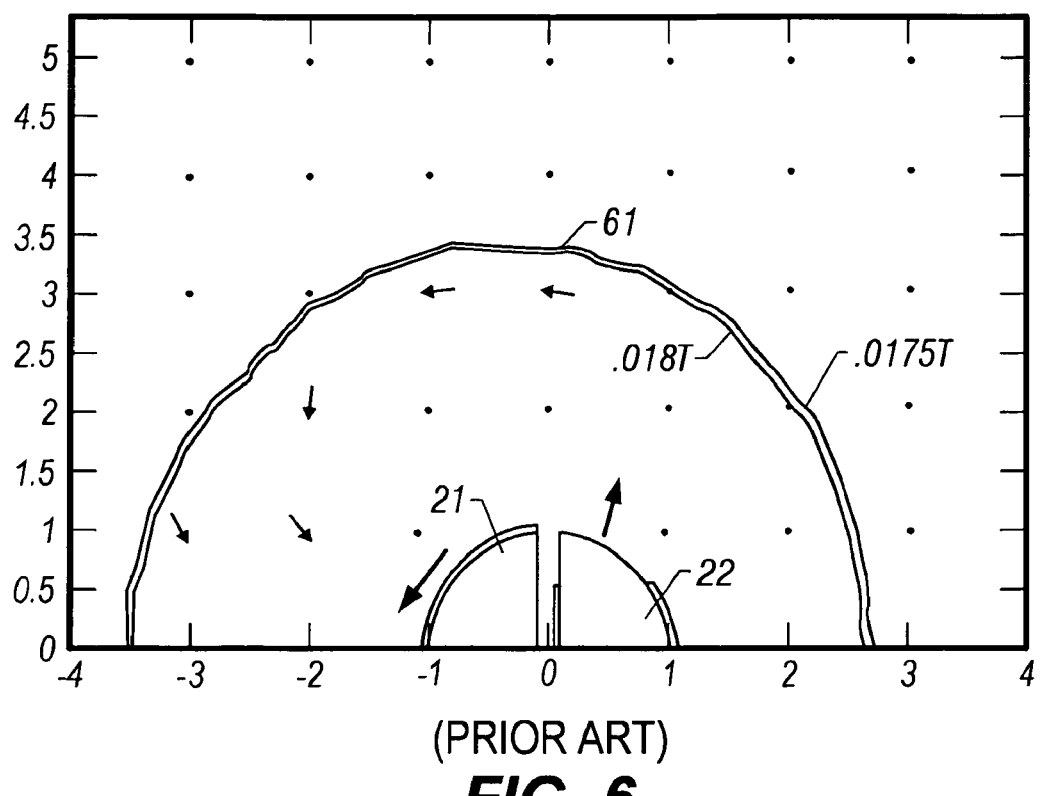
FIG. 6 (prior art) is a plot of two isolines for the static field generated by the probe geometry of FIG. 1 without utilizing a powdered soft magnetic core.

FIG. 3 illustrates the isoline for the probe RF field when using the preferred soft magnetic material in the probe geometry of FIG. 2. FIG. 4 illustrates the isoline 41 for the static magnetic field, when using the preferred magnetic material in the core 22 of the preferred probe geometry of FIG. 2. The distances shown in FIGS. 3 and 4 are normalized to a NMR probe cross sectional radius of 2". Isolines for field strengths of 0.021 T and 0.0205 T are shown in FIG. 4. FIGS. 5 and 6 illustrate the isolines for the static magnetic field 51 and the RF magnetic field 61 respectively, for the probe geometry of FIG. 2, without using the preferred powdered soft magnetic material in core 22. Isolines for field strengths of 0.066 T are shown in FIG. 5 while isolines for a field strength of 0.018 T and 0.0175 T are shown in FIG. 6. Comparison of the static magnetic field and RF magnetic field isolines of FIGS. 3 and 4 to the static magnetic field and RF magnetic field isolines of FIGS. 5 and 6, demonstrates an improvement by a factor of 3 in the RF antenna efficiency and magnet field enhancement, for the probe design of FIG. 2 using the preferred powdered soft magnetic core material. The reciprocity principle suggests that the probe of FIG./2, using a soft magnetic material core, provides a three-fold gain in probe sensitivity in the receiving mode as well.

Figure 7:
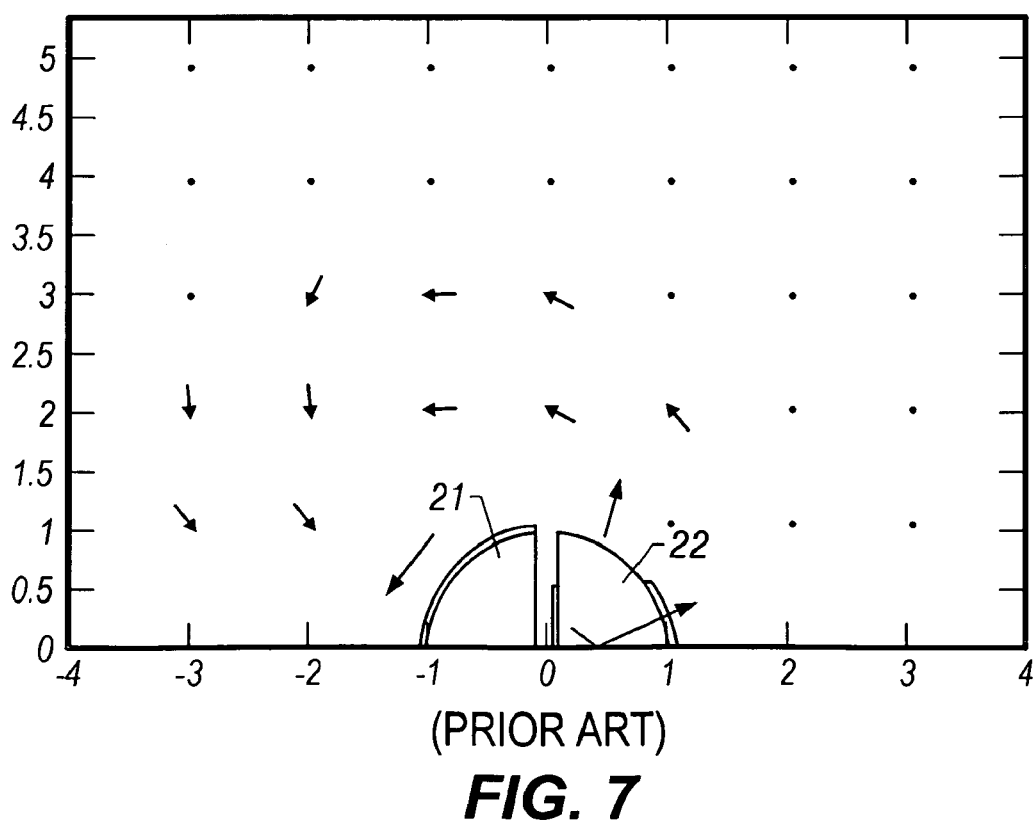
FIG. 7 (prior art) illustrates the isolines for the magnetic flux density of the static field exceeding 0.35 T illustrating that no contour lines appear at the antenna core region.
Figure 8:
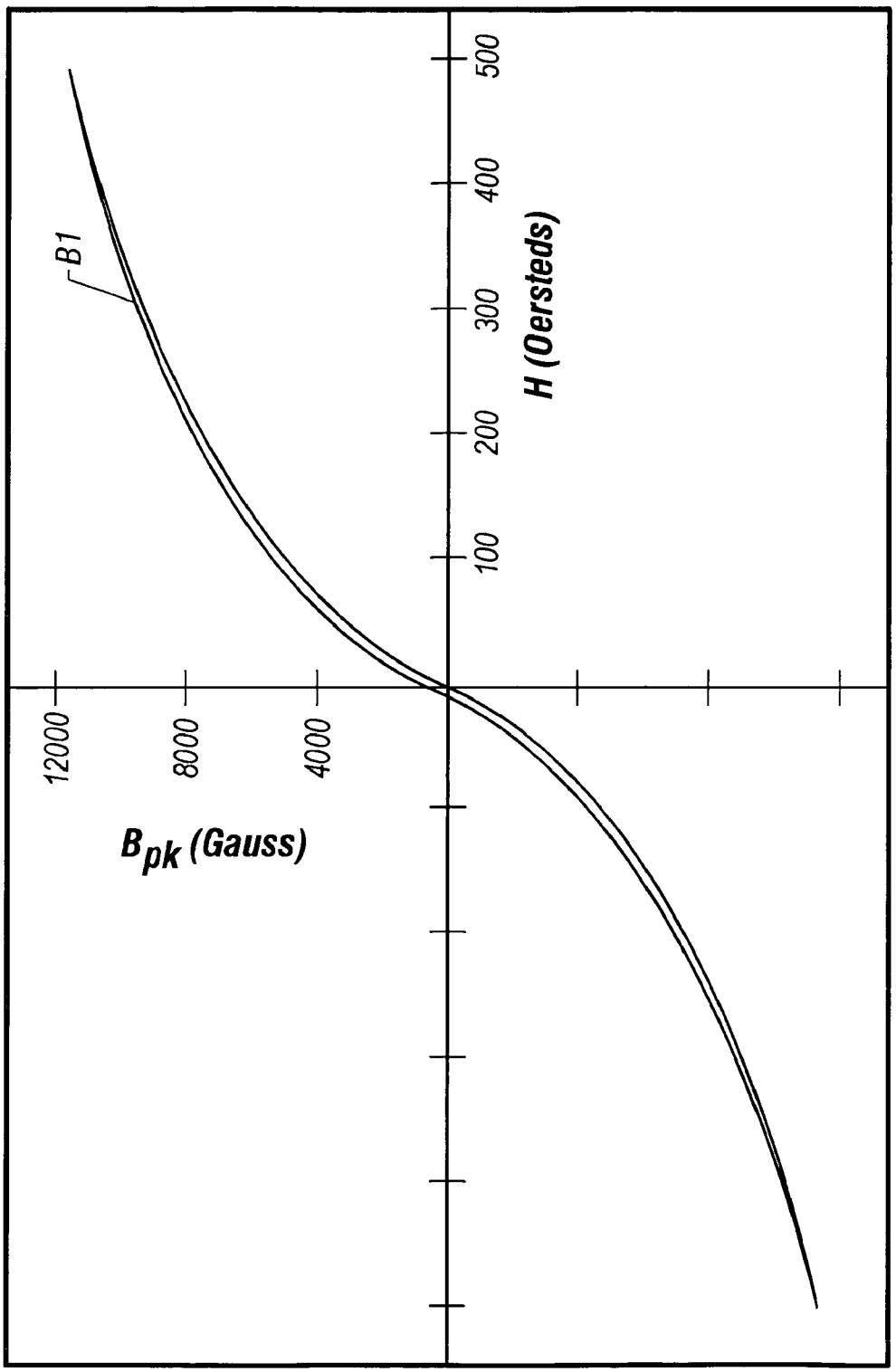
FIG. 8 (prior art) illustrates the flux density value of 0.35 T as well below the saturation flux density of typical iron powdered soft magnetic materials.

FIG. 7 is a plot that was generated to show isolines for the magnetic flux density of the static magnetic field exceeding 0.35 T. None are seen. As it is clear from FIG. 8, presenting the magnetic hysteresis curve B1 for the preferred core material, the flux density value of 0.35 T is well below the saturation flux density of the preferred core soft magnetic iron powder materials which is about 1.2 T. This value typically exceeds the maximum flux density near the surface of the strongest permanent magnets (e.g., Sm2 Co17), thereby enabling a new variety of geometric core designs, not previously useful in core designs, which required compensation for the limitations of ferrite cores.

Figure 9:
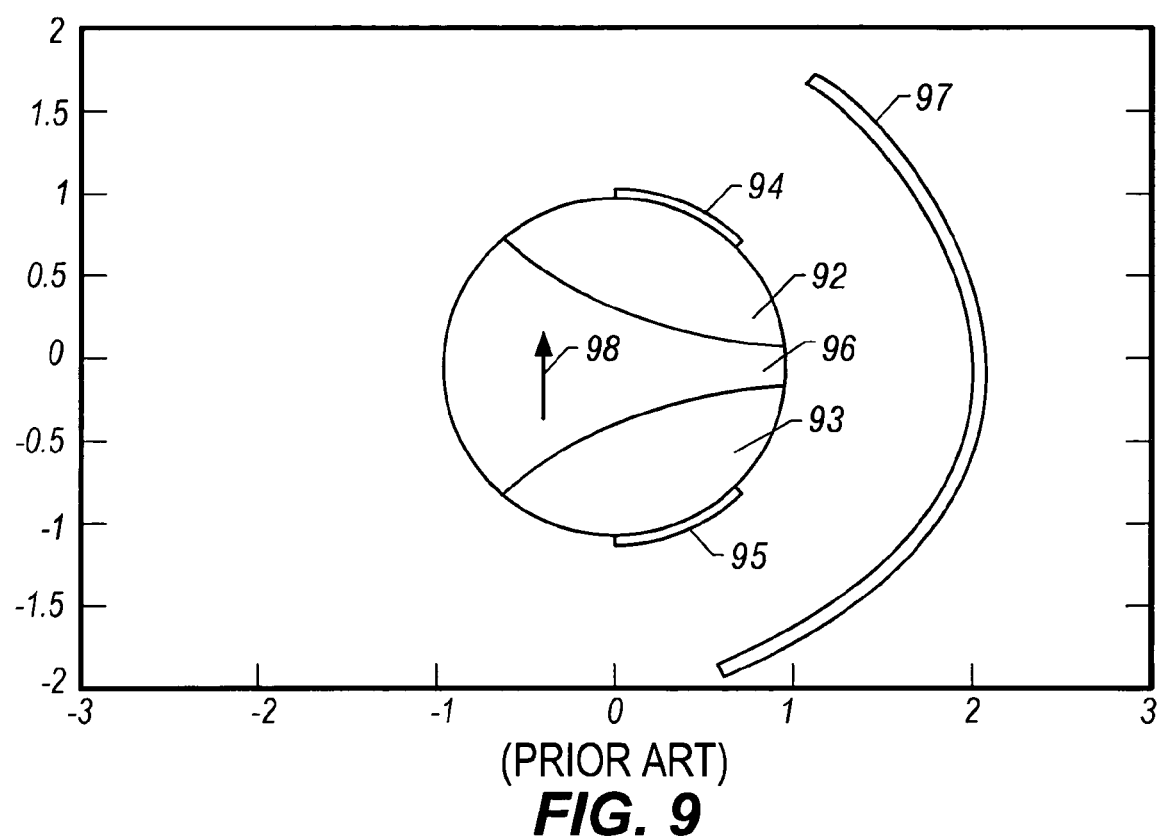
FIG. 9 (prior art) is an illustration of an alternative embodiment of the present invention.

FIG. 9 illustrates an alternative embodiment of the present invention having two cores 92 and 93 and magnet 96. Antenna flat wires 94 and 95 are located adjacent cores 92 and 93, respectively. Magnet 96 has magnetic dipole 98. Preferably both cores are made of the preferred soft core material. The antenna assembly of FIG. 9 generates a RF magnetic field perpendicular to the magnetic field of the permanent magnet in the area in front of the probe in sensitive volume 97.

The limiting eqns. (1) and (2) and other geometric considerations, as well as the maximum effective permeability, as discussed in connection with use of the preferred powdered soft magnetic core material and core shape of FIG. 2, also apply to the alternative embodiment of the probe shown in FIG. 9.

In the preferred embodiment, as shown in FIG. 2, the antenna dipole moment is perpendicular to a line between an effective center of the magnet dipole moment and an effective center of the antenna dipole moment. In the alternative embodiment of FIG. 9, the permanent magnet has a magnetic dipole moment in a plane perpendicular to the axes of elongation and the antenna assembly has a dipole moment in a plane perpendicular to the axes of elongation and parallel to a line between the effective center of the magnet dipole moment and the effective center of the antenna dipole moment. In another alternative embodiment, the permanent magnet has a magnetic dipole moment in a plane perpendicular to the axes of elongation, the antenna assembly has a dipole moment in a plane perpendicular to the axes of elongation and the antenna dipole moment and the magnet dipole moment have coincident effective centers.

In addition to improving antenna efficiency, the flux concentration effect of the preferred powdered soft magnetic core provides the additional significant consequence of rendering the antenna assembly relatively insensitive to the conductivity of the permanent magnet. This insensitivity enables the use of relatively powerful conductive magnets, for example SmCo, to establish a larger static magnetic field, increasing the NMR signal and NMR signal-to-noise ratio.

The preferred powdered core material also reduces or substantially eliminates magnetostrictive ringing by virtue of the particulate structure of the preferred material. The magnetic particle size of the preferred core material (powder) is substantially smaller than the minimum wavelength for acoustic excitation associated with magnetostrictive ringing. Moreover, the epoxy binder does not efficiency transmit acoustic energy between particles.

The preferred powdered core magnetic and electrical characteristics are more stable than ferrite core characteristics in presence of temperature variations. This temperature stability is due to the fact that the magnetic and electrical characteristic of the preferred core is determined mainly by the shape of the core and the micro-geometry of the particulate structure (particle shape and volume packing density) of the preferred powdered material and substantially independent of the material of the particles.

Using magnetic materials in the antenna as a magnetic core could cause problems with magneto-acoustic excitation due to the effect of magnetostriction. In ferromagnetic materials, there is a coupling between the elastic quantities and magnetism leading to a dependence of elastic energy on the magnetization of the material. This dependence results in a stress (and strain) when magnetization of the material changes. The stress is initially generated in the transmit mode of the antenna operation. The effect is most noticeable but not limited to the situation where the generated stress has the frequency of an acoustic resonance of a structural element of the soft magnetic core. Even without acoustic resonance during the RF pulse an acoustic wave packet is transmitted. This travels along the body of the NMR tool and gets reflected at mechanical interfaces. Therefore, at various times, a reflected acoustic wave packets arrive back at the NMR sensor coil and cause interference. Conversely, if stress is applied to an unsaturated crystal, the local magnetization will change direction (and in most cases, the bulk magnetization will change its magnitude) in order to reduce the stress energy through the action of magnetostrictive strain. The change of magnetization corresponding to the oscillating stress will induce a spurious signal in the NMR antenna during the process of receiving the NMR spin echo signals.

Figure 10:
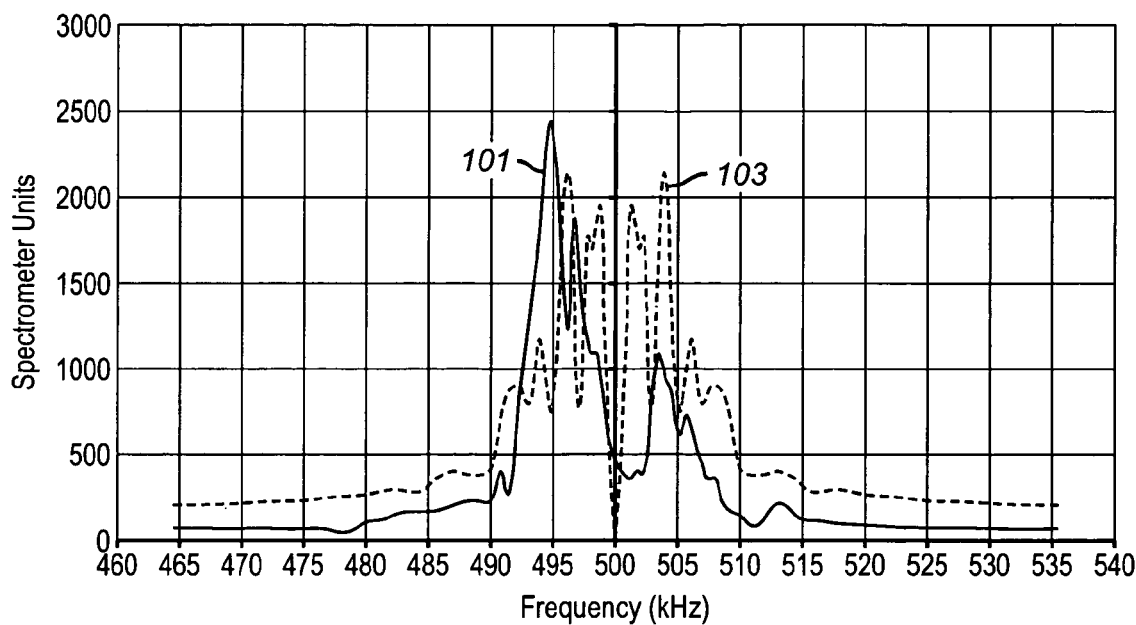
FIG. 10 shows the results of a ringing test of NMR probes using a ferrite flux guide as part of the antenna assembly.

Turning now to FIG. 10, shown are two sets of experimental data 101 and 103 showing the spectral ringing of a ferrite flux guide. The abscissa is frequency (ranging from 460 kHZ to 540 kHz) while the ordinate is the amplitude of the spectra in arbitrary units. The ringing is noticeable in the spectral band from about 490 kHz to 510 kHz. The ferrite for which data are shown in FIG. 10 has a high level of magnetostrictive ringing, which is quite normal for ferrite material.

Figure 11:
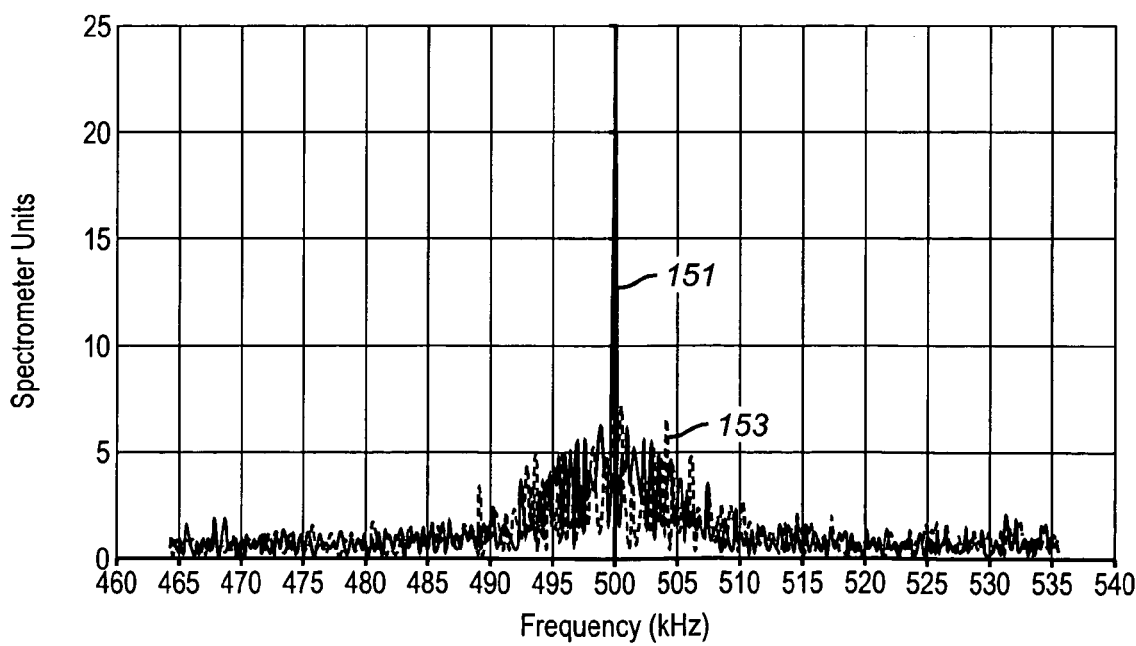
FIG. 11 shows the results of a ringing test of NMR probes using an amorphous metal ribbon and Fluxtrol™.

Similar sets of experimental data are shown in FIG. 11 for two different materials that are characterized by a low level of magnetostrictive ringing. The curve 151 corresponds to a stack of amorphous metal ribbons (discussed below) while the curve 153 is for the material Fluxtrol® (#17) that is a powdered soft magnetic material of the type discussed above. It should be pointed out that the vertical scale in FIG. 11 is from 0–25 units: this is much smaller than the range in FIG. 10 that is from 0–3000 arbitrary units. These data show that the stack of amorphous metal ribbons and soft magnetic materials have a level of ringing that is two orders of magnitude less than ferrite.

It should be noted that Fluxtrol™ has been used in the past, primary as flux concentrators for induction heating. This is brought out by the Fluxtrol® document downloaded from the website for Fluxtrol Manufacturing Company. What follows includes a discovery of a novel use for the material.

Figure 12:
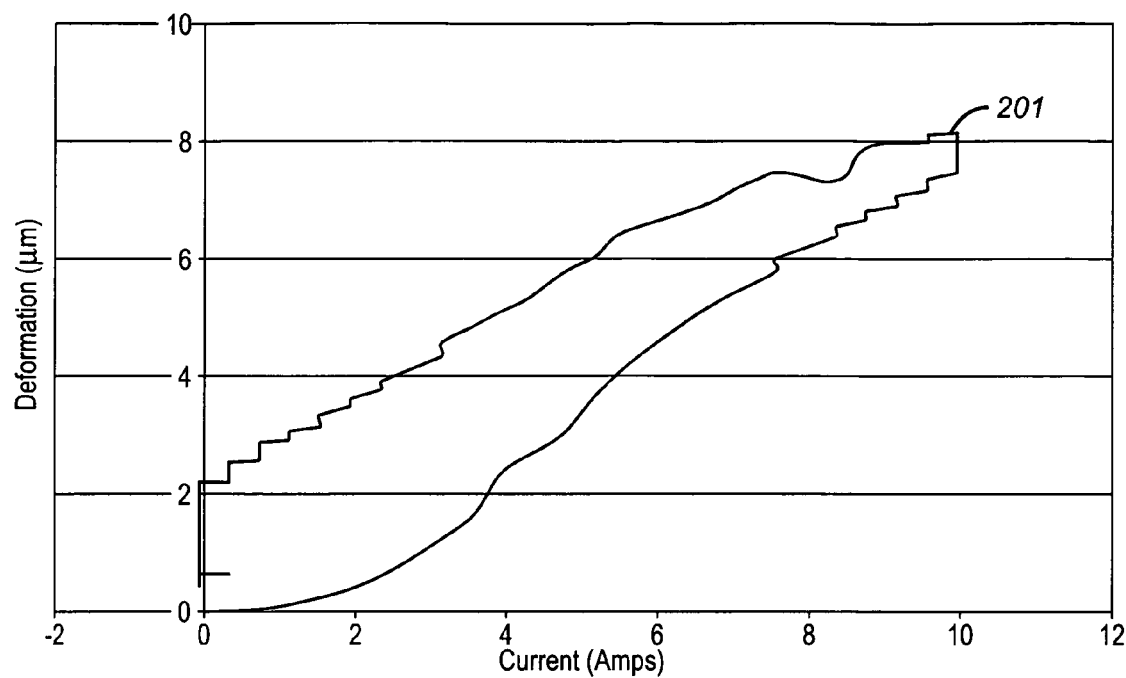
FIG. 12 shows the magnetostrictive hysteresis associated with Fluxtrol™.

Turning now to FIG. 12, a hysteresis curve 201 for a Fluxtrol® is shown. The abscissa is the current applied to a coil enclosing a sample of the material and the ordinate is the magnetostrictive deformation produced (in μm). The arrows in FIG. 12 show that as the current is increased, the deformation is increased, but upon reducing the current, some residual deformation will remain. The large area within the hysteresis curve is an indication of high internal dissipation and damping. This is much larger than the hysteresis curve for a steel core shown in FIG. 13.

Figure 13:
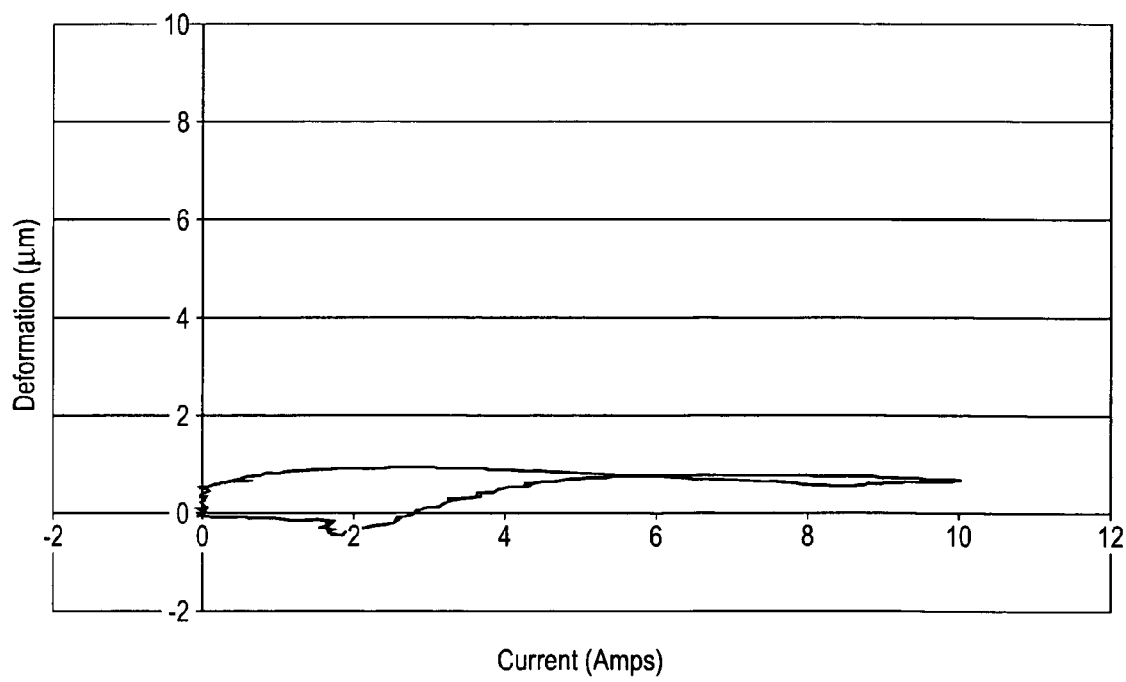
FIG. 13 shows the magnetostrictive hysteresis associated with steel.

Turning now to FIG. 13, a hysteresis curve for steel is shown. The scales in FIG. 13 are the same as the scales in FIG. 12., making it clear that there would be very little internal damping of acoustic waves in steel.

Typical metals used in soft magnetic cores have an acoustic wave velocity of the order of 6 km/s. At an RF frequency of 500 kHz, this gives a wavelength for acoustic waves of approximately 12 mm. In order to reduce intragranular electromagnetic RF losses, the grain sizes used in powdered cores are of the order of 0.01–0.1 mm. Hence selecting the grain size to minimize RF dissipation also makes the grain size much smaller than half the acoustic wavelength.

A second requirement is that the binding material should also provide electrical insulation and acoustic decoupling between metal particles. The necessity of having a sufficient quantity of binding material to provide electrical insulation and acoustic decoupling leads to a relatively low magnetic permeability. This low magnetic permeability limits the use of such materials to core configurations having a high demagnetization factor, e.g., as antenna cores.

We next discuss amorphous metals as fluxguides. Cooling certain molten metal alloys extremely rapidly to the solid state makes an amorphous metal. This material has specific properties depending on the actual composition of the alloy. Some of the materials such as METGLAS® 2705M from Allied Signal Inc. provide high magnetic permeability combined with low magnetostriction. Due to the manufacturing process it is only available in ribbons of about 2 inch times 0.8 mil. In a preferred embodiment of the invention, a flux guide of a NMR antenna comprising a stack of amorphous metal ribbons with non-conductive interlayers is used. The interlayer should isolate the ribbons from each other and provide high acoustic damping and should absorb the remaining magnetostrictive ringing. In order to avoid eddy currents, the stack of laminates should be oriented in such a way that high frequency field lines do not cross the amorphous ribbon. A flux guide, of the type for which test results are shown in FIG. 11, is made of a stack of METGLAS® 2705M with Kapton® interlayer. Kapton® is a registered trademark of DuPont that generally covers a variety of polyimide films.

Amorphous metals and, specifically METGLAS® have been used in prior art as antenna cores. Examples of these are given in U.S. Pat. Nos. 5,220,338 and 5,220,339 to Muatshushita. However, their use as antenna cores for an NMR apparatus and method with reduced magnetostrictive ringing are believed to be novel.

The present invention has been discussed above using a wireline logging tool of Reiderman as an example. The present invention is equally applicable for use with Measurement-while-drilling logging (MWD) tools. For example, U.S. Pat. No. 6,215,304 to Slade teaches the use of ferrite members for an antenna core for MWD applications. As discussed therein, the core has to be split up into a plurality of separate members with gaps in-between to avoid resonance effects. Instead of gapped ferrite elements, materials of the present invention may be used in a preferred embodiment of a MWD NMR logging tool such as that of Slade.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A nuclear magnetic resonance (NMR) logging apparatus configured for use in a borehole and configured for determining properties of an earth formation surrounding the borehole, the apparatus comprising:
   (a) a magnet which induces a static magnetic field in a region of interest in the earth formation;
   (b) a transmitting antenna assembly which generates a radio frequency magnetic field within said region of interest and thereby produces NMR signals from materials in the region of interest; and
   (c) a receiving antenna assembly which detects said NMR signals from said region of interest; wherein at least one of the antenna assemblies includes at least one magnetic core formed from a material having a particulate structure with a particle size which substantially eliminates magnetostrictive ringing.

2. The NMR logging apparatus of claim 1 wherein said core material comprises a powdered soft magnetic material.

3. The NMR logging apparatus of claim 2 wherein the powdered soft magnetic core material is non-conductive and has a maximum grain size which substantially reduces intragranular power loss at a frequency of said radio frequency magnetic field.

4. The NMR logging apparatus of claim 2 wherein the powdered soft magnetic core material has a maximum grain size which is less than half a wavelength of an acoustic wave having a frequency at the frequency of said radio frequency magnetic field.

5. The NMR logging apparatus of claim 1 wherein said core material has a large area within a hysteresis loop associated with magnetostrictive deformation of the core material.

6. The NMR logging apparatus of claim 2 wherein said at least one antenna assembly has a core further comprises a non-conductive bonding agent having substantial acoustic decoupling between grains of the powdered soft magnetic material.

7. The NMR logging apparatus of claim 1 wherein said logging apparatus is configured to be conveyed on one of (i) a wireline, and, (ii) a drilling tubular.

8. The NMR logging apparatus of claim 1 wherein the transmitting antenna assembly and the receiving antenna assembly are the same.

9. A method of determining properties of an earth formation surrounding a borehole, the method comprising:
   (a) using a magnet on a nuclear magnetic resonance (NMR) logging apparatus conveyed in the borehole in order to induce a static magnetic field in a region of interest in the earth formation;
   (b) using a transmitting antenna assembly in order to induce a radio frequency magnetic field within said region of interest and producing NMR signals from materials in the region of interest; and
   (c) using a receiving antenna assembly in order to detect said NMR signals from said region of interest;
   the method further comprising using a core in at least one of the antenna assemblies wherein the core is formed from a material having a particular structure with a particle size which substantially eliminates magnetostrictive ringing.

10. The method of claim 9 further comprising using a powdered soft magnetic material as said core material.

11. The method of claim 10 further comprising selecting the powdered soft magnetic material of the core to be substantially non-conductive and to have a maximum grain size which substantially reduces intragranular power loss at a frequency of said radio frequency magnetic field.

12. The method of claim 10 further comprising selecting as the powdered soft magnetic core material, a core material having a maximum grain size less than half a wavelength of an acoustic wave having a frequency of said radio frequency magnetic field.

13. The method of claim 10 further comprising selecting said core material that has a large area within a hysteresis loop associated with a magnetostrictive deformation of the core material.

14. The method of claim 10 further comprising using in said at least one antenna assembly, a powdered soft magnetic core of a non-conductive bonding agent having substantial acoustic decoupling between grains of the powdered soft magnetic material.

15. The method of claim 10 further comprising conveying said NMR logging apparatus into said borehole on one of (i) a wireline, and, (ii) a drilling tubular.

* * * * *